United States Patent
Bhullar et al.

(10) Patent No.: US 6,627,057 B1
(45) Date of Patent: Sep. 30, 2003

(54) MICROSPHERE CONTAINING SENSOR

(75) Inventors: Raghbir Singh Bhullar, Indianapolis, IN (US); Brian Hill, Indianapolis, IN (US)

(73) Assignee: Roche Diagnostic Corporation, Indianapolis, IN (US)

( * ) Notice: Subject to any disclaimer, the term of this patent is extended or adjusted under 35 U.S.C. 154(b) by 0 days.

(21) Appl. No.: 09/471,571

(22) Filed: Dec. 23, 1999

(51) Int. Cl.⁷ .............................. G01N 27/327
(52) U.S. Cl. .................. 204/403.01; 204/416; 204/409
(58) Field of Search .................. 204/403, 416, 204/409, 415, 419, 403.01, 403.1

(56) References Cited

U.S. PATENT DOCUMENTS

| | | | |
|---|---|---|---|
| 3,847,553 A | 11/1974 | Verbeck | |
| 3,993,451 A | 11/1976 | Verbeck | |
| 4,477,575 A | 10/1984 | Vogel et al. | |
| 4,557,900 A | 12/1985 | Heitzmann | |
| 4,810,470 A | 3/1989 | Burkhardt et al. | |
| 4,946,705 A | 8/1990 | Manning et al. | |
| 4,994,238 A | 2/1991 | Daffern et al. | |
| 5,106,647 A | 4/1992 | Manning et al. | |
| 5,227,042 A | 7/1993 | Zawodzinski et al. | |
| 5,385,846 A | 1/1995 | Kuhn et al. | |
| 5,421,981 A * | 6/1995 | Leader et al. | 204/409 |
| 5,576,073 A | 11/1996 | Kickelhain et al. | 427/555 |
| 5,593,739 A | 1/1997 | Kickelhain | 427/555 |
| 5,708,247 A | 1/1998 | McAleer et al. | |
| 5,756,415 A | 5/1998 | Takahashi et al. | |
| 5,869,345 A | 2/1999 | Chandler | |
| 5,916,156 A | 6/1999 | Hildenbrand et al. | |
| 5,948,695 A | 9/1999 | Douglas et al. | |
| 5,951,836 A | 9/1999 | McAleer et al. | |
| 5,955,179 A | 9/1999 | Kickelhain et al. | 428/210 |
| 5,989,624 A * | 11/1999 | Kida et al. | 427/125 |

FOREIGN PATENT DOCUMENTS

| | | | |
|---|---|---|---|
| JP | 403160358 A | * | 7/1991 |
| JP | 10-113200 | | 5/1998 |
| WO | 0 255 291 | | 7/1987 |
| WO | 98/22824 | | 5/1998 |
| WO | 0 895 084 | | 2/1999 |
| WO | 99/13101 | | 3/1999 |

OTHER PUBLICATIONS

JAPIO abstract of Okuma (JP403160358A).*

* cited by examiner

Primary Examiner—T. Tung
Assistant Examiner—Alex Noguerola
(74) Attorney, Agent, or Firm—Brinks Hofer Gilson & Lione

(57) ABSTRACT

A sensor strip comprises an electrode substrate, an electrode set, on the electrode substrate, and microspheres. The sensor strip allows for a smaller sample volume and maintain a more uniform flow profile through the sample channel.

14 Claims, 2 Drawing Sheets

MICROSPHERE CONTAINING SENSOR

BACKGROUND OF THE INVENTION

The present invention relates to a microsphere containing electrochemical sensor.

Electrochemical biosensors are well known. They have been used to determine the concentration of various analytes from biological samples, particularly from blood. Electrochemical biosensors are described in U.S. Pat. Nos. 5,413,690; 5,762,770 and 5,798,031; as well as in International Publication No. WO99/13101, each of which are hereby incorporated by reference.

An electrochemical biosensor typically includes a sensor strip and a sensor instrument. The sensor strip includes a space that holds the sample to be analyzed, may include reagents to be released into the sample, and includes an electrode set. The electrode set normally includes an insulating substrate, and electrodes that contact the sample, which have contact pads for electrically connecting the electrodes to the sensor instrument. The region of the electrodes where sample analysis actually takes place, the sensing region, typically receives the sample from the top, or from the side via a capillary channel defined by substrate and a cover on the substrate. Often, a reagent is present on the sensing region, to aid in electrochemical analysis. The reagent dissolves into the sample on contact.

Numerous methods have been used for controlling flow and enhancing performance of in vitro diagnostic devices. Birch and Burns (EP 0255291) described the use of a thin (ca. 200 micron) reaction zone over an electrochemical cell to measure analyte concentrations. Numerous inventions based on porous and bibulous (sample-carrying or -filtering) matrices have been described (e.g., Vogel et al. U.S. Pat. No. 4,477,575; Burkhardt et al. U.S. Pat. No. 4,810,470; Daffern et al. U.S. Pat. No. 4,994,238; Kuo et al. EP 0895084; Kuhn, Ochs and Morris U.S. Pat. No. 5,385,846; Douglas et al. U.S. Pat. No. 5,948,695). Hildenbrand et al. (U.S. Pat. No. 5,916,156) disclosed the use of a porous graphite web as a counter electrode and a sample capillary, separated from the working electrode by a non-conductive porous matrix. Hughes and Chambers (WO 9913101) disclose the use of a mesh layer to transport sample and partially occlude a sample chamber, thereby reducing the required sample volume. McAleer et al. (U.S. Pat. Nos. 5,708,247, 5,951,836) described the use of fillers containing both hydrophobic and hydrophilic surface regions to form a network, thereby reducing biosensor sensitivity to hematocrit and temperature.

An amount of sample sufficient to contact the sensing region and fill the path to the sensing region (i.e., a capillary channel) is necessary for analysis with a sensor strip. The amount of sample available for analysis is often small, and especially is the case of blood, it is desirable to minimize the amount of sample necessary. Accordingly, it would be desirable to minimize the volume of sample needed.

SUMMARY OF THE INVENTION

In one aspect, the invention is a sensor strip, including an electrode substrate, an electrode set, on the electrode substrate, and microspheres.

In another aspect, the invention is a method of making a sensor strip, including forming an electrode set on an electrode substrate; forming a channel leading to the electrode set; and inserting microspheres into the channel.

As used herein, the phrase "electrode set" is a set of at least two electrodes, for example 2 to 60, or 3 to 20, electrodes. These electrodes may be, for example, a working electrode, a counter electrode, and a reference electrode.

As used herein, the term "microspheres" is a plurality of particles, but does not require that the particles are spheres; rather they may have any shape. Furthermore, the term "microspheres" also does not limit the size of the particles; they may be any size suitable to fit a plurality onto the sensing region of a sensor strip, or into a channel leading to the sensing region of a sensor strip.

Other features and advantages of the present invention will become apparent from the following detailed description. It should be understood, however, that the detailed description and the specific examples, while indicating embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
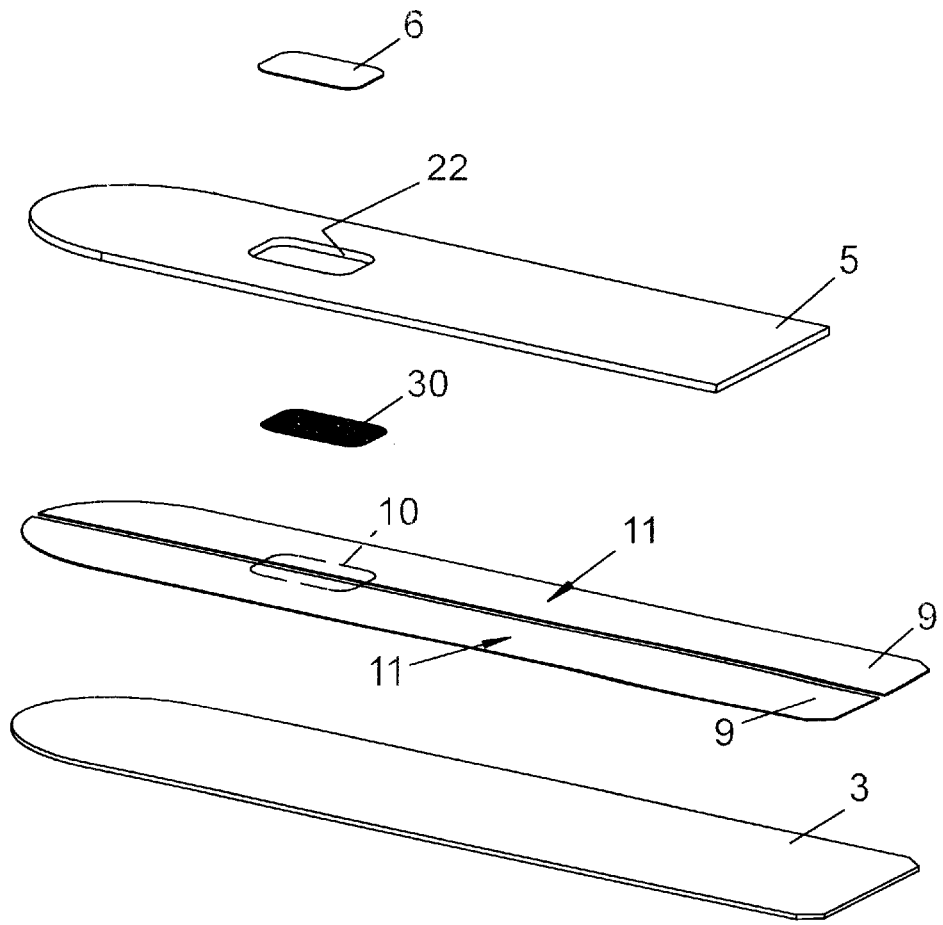
FIG. 1 is an exploded view of an embodiment of a sensor strip of the invention.
Figure 2:
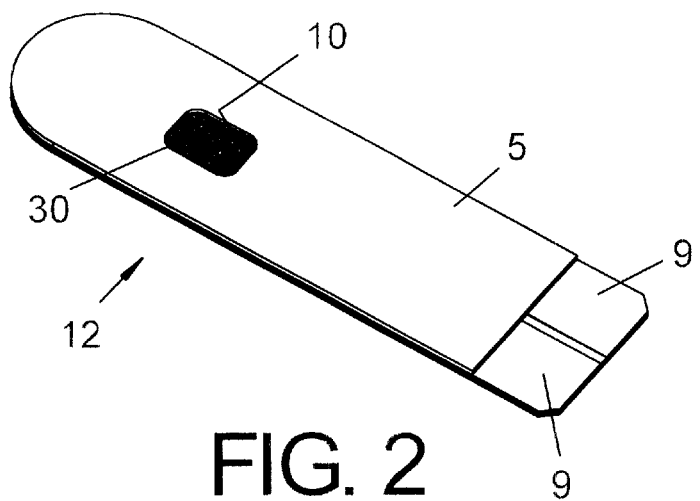
FIG. 2 is a top view of an embodiment of a sensor strip of the invention.

FIG. 2 is a top view of an embodiment of a sensor strip 12, and FIG. 1 is an exploded view. Illustrated in FIG. 1 are an electrode substrate 3, the contact pads 9 and 9, and sensing region 10, all of which are part of the electrodes 11 and 11. The electrodes are, in part, covered with a dielectric 5 exposing the sensing region 10, through hole 22 in the dielectric, and the contact pads 9 and 9. Microspheres 30 are in the space defined by hole 22. Reagent 6 is on the sensing region 10 and on the microspheres 30. In this embodiment, the sample (not shown) is loaded from the top of the sensor strip via hole 22, causing the sample to pass over the microspheres 30.

Figure 3:
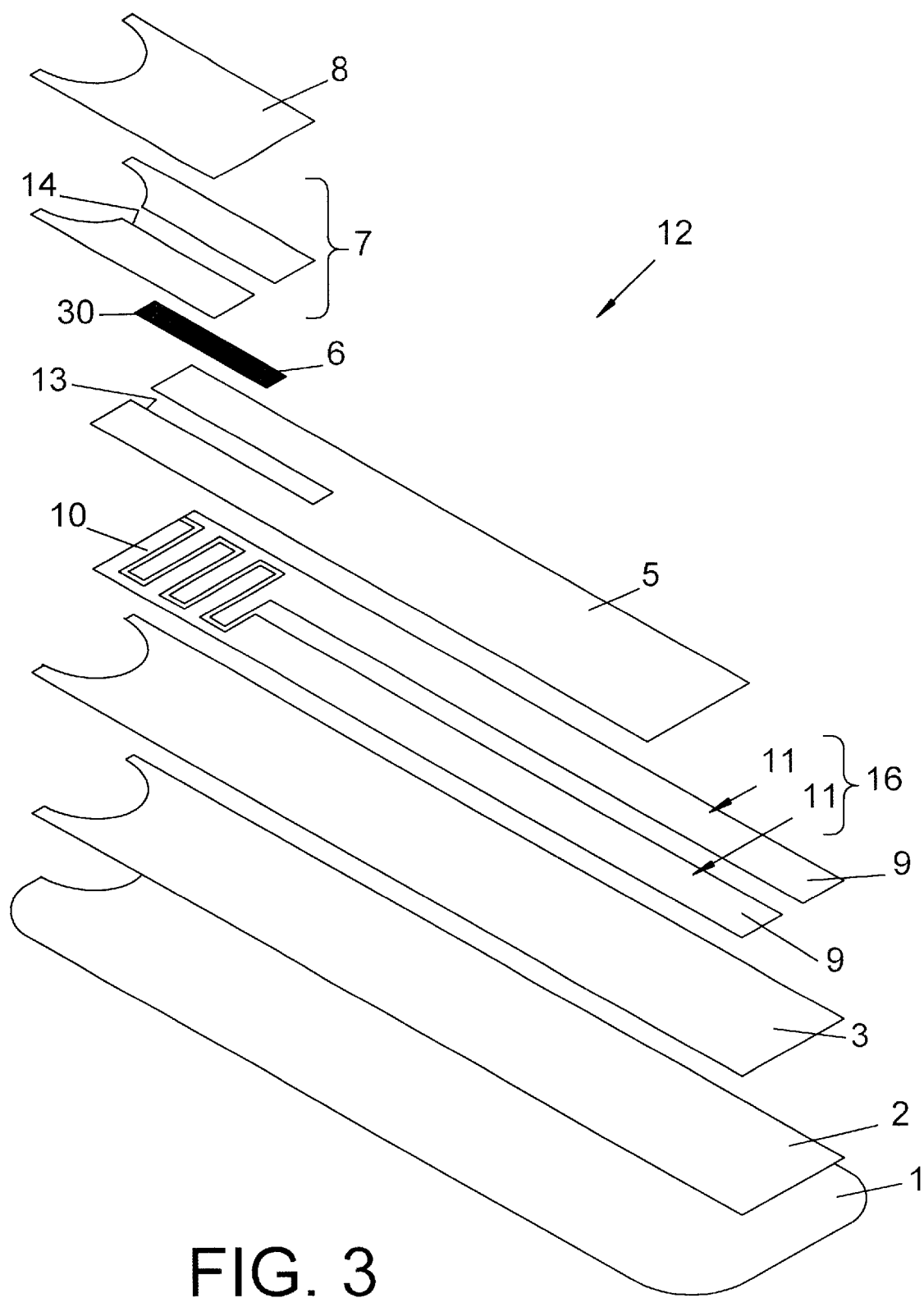
FIG. 3 illustrates an exploded view of another embodiment of a sensor strip of the invention.

FIG. 3 illustrates an exploded view of another embodiment of a sensor strip 12, which includes a base 1, and adhesive foil 2 for holding the base to the electrode substrate 3. The electrode set 16, which is made up of the two electrodes 11 and 11, is on the electrode substrate 3, and is partially covered by a dielectric 5. A cover 8 is attached to one end of the dielectric with adhesive tape 7. A small gap 13 in the dielectric, and a space 14 in the adhesive tape, together with the cover, base and the electrodes, form a pocket inside of which are microsphere 30, together with the optional reagent 6 used to aid in electrochemically detecting and quantifying an analyte. This pocket draws the fluid to be tested onto the sensing region 10 of the electrodes. Alternatively, the cover may be absent, and the sample may be directly applied onto the microspheres 30.

An electrode set includes at least first and second electrodes. The electrodes are separated by a gap that prevents electrical contact between the two electrodes. In FIG. 3, the sensing region of each electrode includes interdigitating fingers. The sensing region is where the actual electrochemical sensing takes place. In the sensing region only a simple straight gap may separate the electrodes (as illustrated in FIG. 1), or it may be more complex, for example, containing a rectilinear gap, forming a region of interlacing fingers of the two electrodes.

The length of the electrode set is preferably 2.5 to 250 mm, the width is preferably 0.4 to 40 mm, the gap between the contact pads is preferably 1 $\mu$m to 5 mm, and the width of each contact pad is preferably 1 to 20 mm. The electrode pattern is preferably symmetric, however this is not required, and an irregular or asymmetric pattern (or electrode shapes) is possible.

The microspheres are particles that are on the sensing region of the electrodes, and/or are present in a channel through which the sample will pass as it travels to the sensing region. The microspheres are not required to be spheres, but rather may have any shape. Furthermore, the microspheres may be any size suitable to fit a plurality of the microspheres onto the sensing region of a sensor strip, or into a channel leading to the sensing region of a sensor strip.

The microspheres may be made of any material that does not prevent the sensor strip from carrying out it analytical function. Preferably, the microspheres are made of one or more materials that are chemically inert to the sample and any chemicals present during analysis, and are dielectric (non-conductive), such as ceramics or polymers. Examples include glass beads, glass powder, fumed silica, silica beads, silica powder, latex spheres, alumina powder, diamond powder, polyethylene beads, mineral fibers, titanium oxide powder, polymer coated metal particle, and mixtures thereof. The microspheres are not physically attached to each other, and therefore do not include fabrics, fleeces, nor two or three-dimensional networks or honeycomb structures. Rather, once sample is present, each microsphere is physically unattached.

The microspheres provide a microcapillary structure, which may maintain a more uniform flow profile through the channel leading to the sensing region. Furthermore, the microspheres occupy a portion of the volume of the channel, reducing the total amount of sample necessary for analysis. Another advantage is that the thermal mass of the sensor may be increased by the presence of the microspheres, and therefore may result in a more uniform temperature through the duration of the measurement.

The microspheres may be coated by the optional reagent. The high surface area of the microspheres will allow a more even distribution of the reagent to the sample, as the sample passes over the microspheres. The reagent, when present, may help hold the microspheres in place prior to application of the sample, however, the microspheres will not be physically attached to each other once the sample is contacted since the reagent will dissolve or disperse into the sample. Similarly, an optional film forming agent may coat the microspheres, to aid in holding them in place prior to application of the sample, if the film forming agent dissolves or disperses once contacted by the sample, so that the microspheres are not physically attached to each other after application of the sample. Often, the reagent, when present, includes a film forming polymer or component to aid in keeping the reagent on the sensing region; in the present invention, the microspheres allow the amount of the film forming polymer or component to be reduced, and consequently the diffusion coefficients and hydration/dissolution rates increase.

Optionally, the microspheres may have a surface treatment make them more hydrophobic or more hydrophilic. Preferably, the surface is hydrophilic. Also preferably the hydrophobic/hydrophilic nature of the surface of the microspheres is uniform, more preferably the surfaces of the microspheres are homogeneously hydrophilic.

The average diameter of the microspheres must be small enough so that a plurality will fit onto the sensing region of a sensor strip, or into a channel leading to the sensing region of a sensor strip, but is otherwise not limited. Preferably, the microspheres have an average diameter of at most 0.5 mm, more preferably, 1 to 300 m, most preferably 10 to 200 m. Suitable materials include the glass spheres having an average diameter of 178 m sold by Duke Scientific Corp., of Palo Alto, Calif.

The amount of microspheres is not limited, but is preferably at most an amount that can fit in the path or channel which leads to the sensing region. The channel volume is the volume of the path or channel defined at one end by the sensing region, and at the other end by the smallest surface area covering that could seal off the channel. Preferably, the amount of microspheres in the sensor strip is 1 to 99%, more preferably 10 to 90%, including 20%, 30%, 40%, 50%, 60%, 70% and 80%, of the channel volume.

The microspheres may be applied to the sensor strip as a mixture with a liquid, for example water or an organic solvent. The proportion of microspheres to liquid is not limited. For example, it is possible to use a mixture which contains 11 to 99%, or 15 to 90%, or even 20 to 80%, by weight, of microspheres, based on the total weight of the composition.

The method of forming of the remainder of the sensor strip is not limited. Any previous method may be used. For example, the electrodes may be formed by sealing foil onto the electrode substrate (for example, gold foil). The electrodes may be screen printed onto the electrode substrate, or a metallic layer may be sputtered and then electrodes formed in it by lithography. Alternatively, the electrodes may be formed by lamination, or laser ablation as described in application Ser. No. 09/411,940, filed Oct. 4, 1999, and entitled "LASER DEFINED FEATURES FOR PATTERNED LAMINATES AND ELECTRODE", hereby incorporated by reference.

Preferably, the electrode includes gold, platinum, palladium, iridium, or alloys of these metals, since such noble metals and their alloys are unreactive in biological systems. The electrodes may be any thickness, but preferably are 10 nm to 1 mm, more preferably, 20 nm to 100 $\mu$m, or even 25 nm to 1 $\mu$m.

A UV curable dielectric and which is screen printable, may be used to form the dielectric, for example the polymer composition 5018 dielectric composition from DuPont. The clear cover is a clear material that is inert to biological fluids, for example glass, polyethylene, polypropylene, polyvinylchloride, polyimide, or polyester. The clear cover may have markings. The adhesive tape is also a flexible polymer having a surfaces covered with an adhesive; these materials are also well known to those of ordinary skill in the art.

The base is an optional supporting structure, and is preferably made of a flexible polymer material, with a thickness sufficient to provide support to the sensor strip, for example polyester with a thickness of 6 mils. The adhesive foil may be made for the same types of compositions as the adhesive tape.

The reagent is optional, and may be used to provide electrochemical probes for specific analytes. The starting reagents are the reactants or components of the reagent, and are often compounded together in liquid form before application to the ribbons or reels. The liquid may then evaporate, leaving the reagent in solid form. The choice of specific reagent depends on the specific analyte or analytes to be measured, and are well known to those of ordinary skill in the art. For example, a reagent for measurement of glucose in a human blood sample contains 62.2 mg polyethylene oxide (mean molecular weight of 100–900 kilodaltons), 3.3 mg NATROSOL 250 M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase, forming a solution of quinoprotein glucose dehydrogenase. This reagent is described in WO 99/30152, pages 7–10, hereby incorporated by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate butter), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight:volume) Avicel. A further description of the reagent for a hematocrit assay is found in U.S. Pat. No. 5,385,846, the disclosure of which is incorporated herein by reference.

Other non-limiting examples of enzymes and mediators that may be used in measuring particular analytes in cell 10 of the present invention are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate | Diaphorase | Ferricyanide | Phenazine Ethosulfate, |

TABLE 1-continued

| Analyte | Enzymes | Mediator (Oxidized Form) | Additional Mediator |
|---|---|---|---|
| Dehydrogenase | | | or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is appreciated that a variety of electrochemical assays may be conducted with cell 10 in accordance with this disclosure.

The processes and products described include disposable biosensors, especially for use in diagnostic devices. However, also included are electrochemical sensors for non-diagnostic uses, such as measuring an analyte in any biological, environmental, food, or other sample. In addition, a plurality of sensor strips are typically packaged in a vial, usually with a stopper.

What is claimed is:

1. A sensor strip for determining the concentration of an analyte in a biological sample, comprising:
    (a) an electrode substrate,
    (b) an electrode set, on said electrode substrate,
    (c) microspheres, said microspheres comprising glass, silica or latex, and
    (d) a cover on said electrode set, wherein said cover, said electrode set, and said electrode substrate together define a channel, and said microspheres are in said channel.

2. The sensor strip of claim 1, wherein said microspheres are on said electrode set.

3. The sensor strip of claim 2, further comprising:
    (e) reagent on said microspheres.

4. The sensor strip of claim 3, wherein said microspheres have an average diameter of 1 to 300 µm.

5. The sensor strip of claim 2, wherein said microspheres are homogeneously hydrophilic.

6. The sensor strip of claim 1, wherein said microspheres are homogeneously hydrophilic.

7. Packaged sensor strips, comprising:
    a plurality of the sensor strips of claim 1,
    a vial, containing said plurality of said sensor strips, and
    a stopper, sealing said vial.

8. A sensor strip for determining the concentration of an analyte in a biological sample, comprising:
    (a) an electrode substrate;
    (b) an electrode set, on said electrode substrate;
    (c) microspheres;
    (d) a cover on said electrode set, wherein said cover, said electrode set, and said electrode substrate together define a channel, and said microspheres are in said channel, and
    (e) reagent on said microspheres.

9. The sensor strip of claim 8, further comprising:

(f) a dielectric, on said electrode substrate, wherein said dielectric, said cover, said electrode set, and said electrode substrate together define said channel.

10. The sensor strip of claim 8, wherein said microspheres have an average diameter of 1 to 300 μm.

11. A sensor strip, comprising:

(a) an electrode substrate, (b) an electrode set, on said electrode substrate, (c) microspheres, (d) a cover, on said electrode set, and (f) a dielectric, on said electrode substrate, wherein said dielectric, said cover, said electrode set, and said electrode substrate together define a channel, and said microspheres are in said channel.

12. Packaged sensor strips, comprising:

a plurality of the sensor strips of claim 11, a vial, containing said plurality of said sensor strips, and a stopper, sealing said vial.

13. A sensor strip, comprising:

(a) an electrode substrate, (b) an electrode set, on said electrode substrate, (c) microspheres, wherein said microspheres comprise glass, silica or latex, and (d) a cover, on said electrode set, wherein said cover, said electrode set, and said electrode substrate together define a channel, and said microspheres are in said channel.

14. A sensor strip, comprising:

(a) an electrode substrate, (b) an electrode set, on said electrode substrate, (c) microspheres, (d) a cover on said electrode set, wherein said cover, said electrode set, and said electrode substrate together define a channel, and said microspheres are in said channel, and (e) reagent on said microspheres.

* * * * *